US00PP19728P2

(12) United States Plant Patent
Heinrich

(10) Patent No.: US PP19,728 P2
(45) Date of Patent: Feb. 17, 2009

(54) *SCAEVOLA* PLANT NAMED 'WESSCAETOWHI'

(50) Latin Name: *Scaevola aemula*
Varietal Denomination: Wesscaetowhi

(75) Inventor: Westhoff Heinrich, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 11/983,739

(22) Filed: Nov. 12, 2007

(51) Int. Cl.
*A01H 5/00* (2006.01)

(52) U.S. Cl. ..... Plt./363

(58) Field of Classification Search ..... Plt./363
See application file for complete search history.

(56) References Cited

PUBLICATIONS

UPOV–Rom Gtitm, Plant Variety Database Jan. 2008, GTI Jouve Retrieval Software, Citation for *Scaevola* 'Wesscaetowhi', one page.*

* cited by examiner

*Primary Examiner*—Annette H Para
*Assistant Examiner*—June Hwu
(74) *Attorney, Agent, or Firm*—C. A. Whealy

(57) ABSTRACT

A new and distinct cultivar of *Scaevola* plant named 'Wesscaetowhi', characterized by its compact and mounded plant habit; freely branching habit; freely flowering habit; and white-colored flowers.

1 Drawing Sheet

Botanical designation: *Scaevola aemula.*
Cultivar denomination: 'Wesscaetowhi'.

BACKGROUND OF THE INVENTION

The present invention relates to a new and distinct cultivar of *Scaevola,* botanically known as *Scaevola aemula,* and hereinafter referred to by the name 'Wesscaetowhi'.

The new *Scaevola* is a product of a planned breeding program conducted by the Inventor in Südlohn, Germany The objective of the breeding program is to create new compact and freely-flowering *Scaevola* cultivars with attractive flower coloration.

The new *Scaevola* originated from a cross-pollination made by the Inventor in Südlohn, Germany in 2003 of a proprietary selection of *Scaevola aemula* identified as code number 03P10, not patented, as the female, or seed, parent with a proprietary selection of *Scaevola aemula* identified as code number 03P00, not patented, as the male, or pollen, parent. The cultivar Wesscaetowhi was discovered and selected by the Inventor as a flowering plant within the progeny of the stated cross-pollination in a controlled environment in Südlohn, Germany in 2004.

Asexual reproduction of the new *Scaevola* by vegetative cuttings in a controlled environment in Südlohn, Germany since 2004, has shown that the unique features of this new *Scaevola* are stable and reproduced true to type in successive generations.

SUMMARY OF THE INVENTION

The cultivar Wesscaetowhi has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wesscaetowhi'. These characteristics in combination distinguish 'Wesscaetowhi' as a new and distinct cultivar of *Scaevola:*

1. Compact and mounded plant habit.
2. Freely branching habit.
3. Freely flowering habit.
4. White-colored flowers.

Plants of the new *Scaevola* can be compared to plants of the female parent selection. Plants of the new *Scaevola* differ from plants of the female parent selection in the following characteristics:

1. Plants of the new *Scaevola* are more compact than plants of the female parent selection.
2. Plants of the new *Scaevola* have smaller leaves than plants of the female parent selection.
3. Plants of the new *Scaevola* have more compact flower clusters than plants of the female parent selection.

Plants of the new *Scaevola* can be compared to plants of the male parent selection. Plants of the new *Scaevola* differ from plants of the male parent selection in the following characteristics:

1. Plants of the new *Scaevola* are more compact than plants of the male parent selection.
2. Plants of the new *Scaevola* have smaller leaves than plants of the male parent selection.
3. Plants of the new *Scaevola* have larger flowers than plants of the male parent selection.

Plants of the new *Scaevola* can be compared to plants of the *Scaevola aemula* cultivar Fancy, disclosed in U.S. Plant Pat. No. 9,867. In side-by-side comparisons conducted in S üdlohn, Germany, plants of the new *Scaevola* differed from plants of the cultivar Fancy in the following characteristics:

1. Plants of the new *Scaevola* had smaller leaves than plants of the cultivar Fancy.
2. Plants of the new *Scaevola* had smaller flowers than plants of the cultivar Fancy.

3. Plants of the new *Scaevola* were more freely flowering than plants of the cultivar Fancy.
3. Plants of the new *Scaevola* and the cultivar Fancy differed in flower color as plants of the cultivar Fancy had blue violet-colored flowers.

Plants of the new *Scaevola* can also be compared to plants of the *Scaevola aemula* cultivar Wesscaecry, not patented. In side-by-side comparisons conducted in Südlohn, Germany, plants of the new *Scaevola* differed from plants of the cultivar Wesscaecry in the following characteristics:

1. Plants of the new *Scaevola* were more compact and mounding than plants of the cultivar Wesscaecry.
2. Plants of the new *Scaevola* were more freely branching than plants of the cultivar Wesscaecry.
3. Plants of the new *Scaevola* had smaller leaves than plants of the cultivar Wesscaecry.
4. Plants of the new *Scaevola* were more freely flowering than plants of the cultivar Wesscaecry.

BRIEF DESCRIPTION OF THE PHOTOGRAPH

The accompanying colored photograph illustrates the overall appearance of the new *Scaevola,* showing the colors as true as it is reasonably possible to obtain in colored reproductions of this type. Colors in the photograph may differ slightly from the color values cited in the detailed botanical description which accurately describe the colors of the new *Scaevola.* The photograph comprises a side perspective view of a typical flowering plant of 'Wesscaetowhi' grown in a container.

DETAILED BOTANICAL DESCRIPTION

The photographs and following observations, measurements and values describe plants grown in Südlohn, Germany in containers in a glass-covered greenhouse during the summer under conditions which closely approximate commercial production. During the production of the plants, day temperatures ranged from about 20° C. to 25° C., night temperatures ranged from about 16° C. to 18° C. and light levels ranged from about 3,000 lux to about 50,000 lux. Plants were about four months old when the photographs and the description were taken. In the description, color references are made to The Royal Horticultural Society Colour Chart, 2001 Edition, except where general terms of ordinary dictionary significance are used.

Botanical classification: *Scaevola aemula* cultivar Wesscaetowhi.

Parentage:

*Female, or seed, parent.*—Proprietary selection of *Scaevola aemula* identified as code number 03P10, not patented.

*Male or pollen parent.*—Proprietary selection of *Scaevola aemula* identified as code number 03P00, not patented.

Propagation:

*Type.*—By vegetative cuttings.

*Time to initiate roots.*—About three to four weeks at 20° C.

*Time to develop roots.*—About four to five weeks at 20° C.

*Root description.*—Fibrous; color, 158A.

*Rooting habit.*—Freely branching; moderately dense to dense.

Plant description:

*Plant form and growth habit.*—Compact and mounded plant habit, Vigorous growth habit.

*Branching habit.*—Freely branching, lateral branches potentially forming at every node.

*Plant height.*—About 13 cm to 19 cm.

*Plant diameter* (*area of spread*).—About 20 cm to 30 cm.

Lateral branch description:

*Length.*—About 14 cm to 19 cm.

*Diameter.*—About 2.5 mm.

*Internode length.*—About 1.7 cm.

*Texture.*—Sparsely pubescent.

*Color.*—146A.

Foliage description:

*Arrangement.*—Alternate, simple; sessile.

*Length.*—About 4.15 cm.

*Width.*—About 2.1 cm.

*Shape.*—Broadly spatulate.

*Apex.*—Acute.

*Base.*—Attenuate.

*Margin.*—Slightly serrated.

*Texture, upper and lower surfaces.*—Slightly pubescent.

*Venation pattern.*—Pinnate, arcuate.

*Color.*—Developing and fully expanded foliage, upper surface: 147A; venation, 146A. Developing and fully expanded foliage, lower surface: 147B; venation, 147A.

Flower description:

*Flower type and shape.*—Zygomorphic, semi-circular, fan-shaped flowers with five petals fused at the base to form a tubular flower throat. Flower throat open along the upper surface exposing reproductive organs. Flowers not fragrant.

*Flower arrangement and quantity.*—Solitary sessile flowers arise from leaf axils. Flowers face mostly outwardly. Freely flowering habit, typically about eight to nine flowers per apical branch.

*Flowering time.*—Plants flower continuously from spring to the autumn in Germany. Flowers typically last about a week on the plant. Flowers not persistent.

*Flower buds.*—Shape: Lanceolate. Length: About 1.8 cm. Diameter: About 2 mm to 2.5 mm. Color: 144A to 144B.

*Flowers.*—Length: About 1.45 cm. Width: About 2.6 cm. Flower throat diameter: About 4 mm. Flower tube length: About 1.2 cm. Flower tube diameter, base: About 2.2 mm.

*Petals.*—Quantity: Five, fused at base. Shape: Broadly oblanceolate to elliptic. Apex: Cuspidate. Margin: Entire. Length, above tube: About 1.4 cm. Width, above tube: About 6 mm. Texture, upper and lower surfaces: Smooth, glabrous. Color: When opening and fully opened, upper surface: Close to 155D; venation, close to 155C; at the base, 6B. When opening and fully opened, lower surface: Close to 155D; venation, 145A to 145D. Throat: N144A to N144B; venation, N144A to N144B. Tube: 145B to 145C; venation, 145B to 145C.

*Sepals.*—Quantity and arrangement: One large and two smaller sepals in a single whorl fused at the base. Length, larger sepal: About 1.8 cm. Length, smaller sepals: About 9 mm. Width, larger sepal: About 6.4 mm. Width, smaller sepals: About 1 mm Shape, larger sepal: Lanceolate. Shape, smaller sepals:

Acicular. Apex, all sepals: Acute. Margin, all sepals: Indented or entire. Texture, upper and lower surfaces: Slightly pubescent. Color, upper surface: 147A. Color, lower surface: 146A.

*Peduncles.*—Length: About 11 cm to 14 cm. Diameter: About 2 mm. Strength: Strong, flexible. Texture: Smooth, glabrous. Color: 146A.

*Reproductive organs.*—Androecium: Stamen quantity per flower: About five. Filament length: About 3 mm to 4 mm. Filament color: 165B to 165C. Anther shape: Ovate. Anther length: About 2 mm. Anther diameter: About 1 mm. Anther color: 6D. Pollen: Moderate. Pollen color: 6D.

*Gynoecium.*—Pistil quantity per flower: One. Pistil length: About 9 mm. Style length: About 5 mm. Style color: 145A to 145B. Stigma shape: Elongate. Stigma color, mature: 145A to 145B. Ovary color: 144A.

*Seeds.*—Seed development has not been observed.

Temperature tolerance: Plants of the new *Scaevola* have been observed to tolerate temperatures from about 5° C. to about 30° C.

Pathogen/pest resistance: Plants of the new *Scaevola* have not been shown to be resistant to pathogens and pests common to *Scaevola*.

It is claimed:

1. A new and distinct *Scaevola* plant named 'Wessca-etowhi' as illustrated and described.

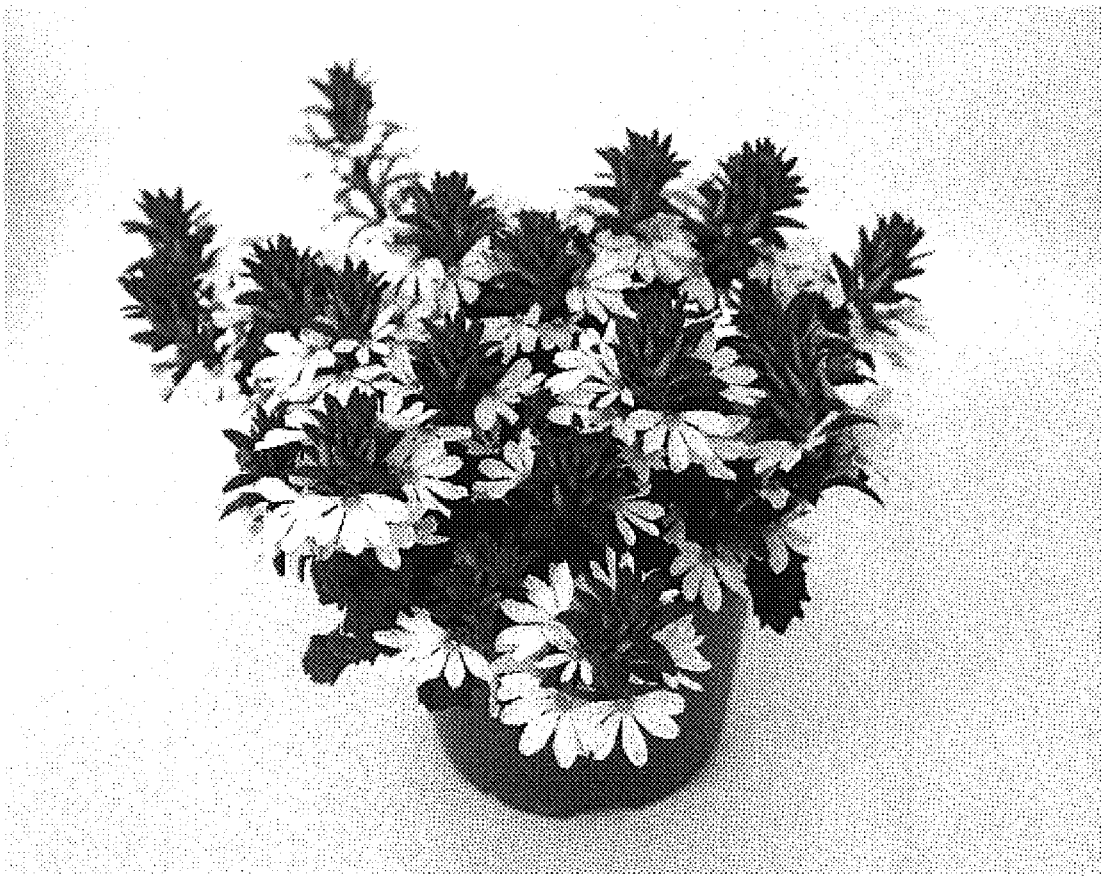

* * * * *